US006194155B1

(12) United States Patent
Cohen

(10) Patent No.: US 6,194,155 B1
(45) Date of Patent: Feb. 27, 2001

(54) COMPUTERIZED METHOD OF IDENTIFYING AND LOCATING RESONATING, SELF-HYBRIDIZING NUCLEIC ACID ELEMENTS

(76) Inventor: Jeffrey Cohen, P.O. Box 651112, Salt Lake City, UT (US) 84165

(*) Notice: Subject to any disclaimer, the term of this patent is extended or adjusted under 35 U.S.C. 154(b) by 0 days.

(21) Appl. No.: 09/305,408

(22) Filed: May 5, 1999

(51) Int. Cl.[7] .......................... C12Q 1/68; G01N 33/48; G01N 33/50; G06F 19/00

(52) U.S. Cl. .................................. 435/6; 702/19; 702/20

(58) Field of Search .................................. 435/6; 702/19, 702/20

(56) References Cited

U.S. PATENT DOCUMENTS 5,028,525 * 7/1991 Gray et al. .............................. 435/6

* cited by examiner

*Primary Examiner*—John S. Brusca
*Assistant Examiner*—Stephen Siu
(74) *Attorney, Agent, or Firm*—Madson & Metcalf

(57) ABSTRACT

The present invention is a computerized method of identifying self-hybridizing sequences in nucleic acid strands. Once the sequences are identified, genetic information frequently residing in or near the sequences can be more easily identified. A computer program is used to automatically and rapidly conduct the steps of the method. Under the method, a practical minimum possible length of a stem sequence is first determined and entered into a program. A maximum loop size is then determined and entered. Subsequently, a mismatch factor is determined as well as whether to include G-T base pairs in total energy calculations. The calculations are then made by identifying a potential upstream stem sequence and iterating through possible downstream stem sequences. Once all possible downstream stem sequences have been compared to the upstream sequence, the upstream sequence is incremented by one base location, and once again all possible downstream sequences are compared. The total number of bonds is calculated using a look-up matrix for every possible combination of downstream and upstream stem sequences. If a sufficient number of possible base pairs exist, together creating sufficient energy for an R-structure to form, the potential R-structure is stored to a file. The R-structure is then analyzed to determine its maximum length. The total located R-structures are then printed out. The located R-structures may also be examined to locate all possible wing structure sequences within each R-structure using a similar iterative process.

15 Claims, 6 Drawing Sheets

| | | A 1 | G 2 | C 3 | T 4 |
|---|---|---|---|---|---|
| A | 1 | 0 | 0 | 0 | 6 |
| G | 2 | 0 | 0 | 7 | 5 |
| C | 3 | 0 | 7 | 0 | 0 |
| T | 4 | 6 | 5 | 0 | 0 |

SEQUENCE LISTING

```
<160> NUMBER OF SEQ ID NOS: 32

<210> SEQ ID NO 1
<211> LENGTH: 40
<212> TYPE: DNA
<213> ORGANISM: Ebola virus

<400> SEQUENCE: 1

cacacaaaaa gaaagaagaa tttttaggat cttttgtgtg                40
```

-continued

<210> SEQ ID NO 2
<211> LENGTH: 58
<212> TYPE: DNA
<213> ORGANISM: Ebola virus

<400> SEQUENCE: 2
gaggaagatt aataattttc ctctcattga aatttatatc ggaatttaaa ttgaaatt 58

<210> SEQ ID NO 3
<211> LENGTH: 33
<212> TYPE: DNA
<213> ORGANISM: Ebola virus

<400> SEQUENCE: 3
taatgatgaa gattaaaacc ttcatcatcc tta 33

<210> SEQ ID NO 4
<211> LENGTH: 34
<212> TYPE: DNA
<213> ORGANISM: Ebola virus

<400> SEQUENCE: 4
gaaaaaccta cctcggctga gagagtgttt tttc 34

<210> SEQ ID NO 5
<211> LENGTH: 41
<212> TYPE: DNA
<213> ORGANISM: Ebola virus

<400> SEQUENCE: 5
gcgatgaaga ttaagccgac agtgagcgta atcttcatct c 41

<210> SEQ ID NO 6
<211> LENGTH: 21
<212> TYPE: DNA
<213> ORGANISM: Ebola virus

<400> SEQUENCE: 6
cctcgtgatc gattcaagag g 21

<210> SEQ ID NO 7
<211> LENGTH: 32
<212> TYPE: DNA
<213> ORGANISM: Ebola virus

<400> SEQUENCE: 7
tttctttggg taattatcct tttccaaaga ac 32

<210> SEQ ID NO 8
<211> LENGTH: 74
<212> TYPE: DNA
<213> ORGANISM: Ebola virus

<400> SEQUENCE: 8
atcaatctag ttatctcttt gagaatgata aacttgatga agattaagaa aaaggtaatc 60
tttcgattat cttt 74

<210> SEQ ID NO 9
<211> LENGTH: 48
<212> TYPE: DNA
<213> ORGANISM: Ebola virus

<400> SEQUENCE: 9

-continued tctcttaaaa tattaagaaa aactgacgga acataaattc tttatgct 48

<210> SEQ ID NO 10
<211> LENGTH: 59
<212> TYPE: DNA
<213> ORGANISM: Ebola virus

<400> SEQUENCE: 10
ttggtattgg ctattgttat attacaatca ataacaagct tgtaaaaata ttgttcttg 59

<210> SEQ ID NO 11
<211> LENGTH: 10
<212> TYPE: DNA
<213> ORGANISM: Ebola virus

<400> SEQUENCE: 11
aagaattttt 10

<210> SEQ ID NO 12
<211> LENGTH: 10
<212> TYPE: DNA
<213> ORGANISM: Ebola virus

<400> SEQUENCE: 12
ataaattctt 10

<210> SEQ ID NO 13
<211> LENGTH: 11
<212> TYPE: DNA
<213> ORGANISM: Ebola virus

<400> SEQUENCE: 13
gaggaagatt a 11

<210> SEQ ID NO 14
<211> LENGTH: 11
<212> TYPE: DNA
<213> ORGANISM: Ebola virus

<400> SEQUENCE: 14
taatcttcat c 11

<210> SEQ ID NO 15
<211> LENGTH: 12
<212> TYPE: DNA
<213> ORGANISM: Ebola virus

<400> SEQUENCE: 15
gaggaagatt aa 12

<210> SEQ ID NO 16
<211> LENGTH: 12
<212> TYPE: DNA
<213> ORGANISM: Ebola virus

<400> SEQUENCE: 16
ttaatcttca tc 12

<210> SEQ ID NO 17
<211> LENGTH: 10
<212> TYPE: DNA
<213> ORGANISM: Ebola virus

<400> SEQUENCE: 17

-continued

```
ttaataattt                                                             10


<210> SEQ ID NO 18
<211> LENGTH: 10
<212> TYPE: DNA
<213> ORGANISM: Ebola virus

<400> SEQUENCE: 18

aaaatattaa                                                             10


<210> SEQ ID NO 19
<211> LENGTH: 11
<212> TYPE: DNA
<213> ORGANISM: Ebola virus

<400> SEQUENCE: 19

gatgaagatt a                                                           11


<210> SEQ ID NO 20
<211> LENGTH: 11
<212> TYPE: DNA
<213> ORGANISM: Ebola virus

<400> SEQUENCE: 20

taatcttcat c                                                           11


<210> SEQ ID NO 21
<211> LENGTH: 10
<212> TYPE: DNA
<213> ORGANISM: Ebola virus

<400> SEQUENCE: 21

aaccttcatc                                                             10


<210> SEQ ID NO 22
<211> LENGTH: 10
<212> TYPE: DNA
<213> ORGANISM: Ebola virus

<400> SEQUENCE: 22

gatgaagatt                                                             10


<210> SEQ ID NO 23
<211> LENGTH: 13
<212> TYPE: DNA
<213> ORGANISM: Ebola virus

<400> SEQUENCE: 23

gatgaagatt aaa                                                         13


<210> SEQ ID NO 24
<211> LENGTH: 13
<212> TYPE: DNA
<213> ORGANISM: Ebola virus

<400> SEQUENCE: 24

tttaatcttc atc                                                         13


<210> SEQ ID NO 25
<211> LENGTH: 11
<212> TYPE: DNA
<213> ORGANISM: Ebola virus
```

-continued

<400> SEQUENCE: 25
aaccttcatc a 11

<210> SEQ ID NO 26
<211> LENGTH: 11
<212> TYPE: DNA
<213> ORGANISM: Ebola virus

<400> SEQUENCE: 26
tgatgaagat t 11

<210> SEQ ID NO 27
<211> LENGTH: 12
<212> TYPE: DNA
<213> ORGANISM: Ebola virus

<400> SEQUENCE: 27
gtaatcttca tc 12

<210> SEQ ID NO 28
<211> LENGTH: 12
<212> TYPE: DNA
<213> ORGANISM: Ebola virus

<400> SEQUENCE: 28
gatgaagatt aa 12

<210> SEQ ID NO 29
<211> LENGTH: 13
<212> TYPE: DNA
<213> ORGANISM: Ebola virus

<400> SEQUENCE: 29
gatgaagatt aag 13

<210> SEQ ID NO 30
<211> LENGTH: 13
<212> TYPE: DNA
<213> ORGANISM: Ebola virus

<400> SEQUENCE: 30
tttaatcttc atc 13

<210> SEQ ID NO 31
<211> LENGTH: 10
<212> TYPE: DNA
<213> ORGANISM: Ebola virus

<400> SEQUENCE: 31
aatcttcatc 10

<210> SEQ ID NO 32
<211> LENGTH: 10
<212> TYPE: DNA
<213> ORGANISM: Ebola virus

<400> SEQUENCE: 32
gaggaagatt 10

COMPUTERIZED METHOD OF IDENTIFYING AND LOCATING RESONATING, SELF-HYBRIDIZING NUCLEIC ACID ELEMENTS

BACKGROUND OF THE INVENTION

1. The Field of the Invention

The present invention relates to self-hybridizing nucleic acid elements which may regulate a number of molecular genetic events. More specifically, the present invention relates to methods of identifying and locating resonating, self-hybridizing nucleic acid elements in a rapid and efficient manner.

2. The Relevant Technology

Proteins are substances which play many roles in living organisms, including regulatory functions. Proteins are polymers made up of subunits called amino acids. There are twenty amino acids which, depending on their arrangement, dictate a protein's biological activity.

In the nucleus and mitochondria of a cell, molecules of deoxyribonucleic acid ("DNA") carry all the information required to make all the proteins required by the body. DNA is a polymer of smaller molecules called nucleotides or bases. There are four nucleotides which comprise DNA—adenine (A), cytosine (C), guanine (G), and thymidine (T). Generally, DNA exists as two polymers or strands (double-stranded) held together by interstrand hydrogen bonds between nucleotides on the two strands. Adenine pairs with thymidine to form hydrogen bonds, and cytosine pairs with guanine. This type of bonding is referred to as Watson and Crick base pairing.

In certain circumstances, the nucleotides in a single molecule of DNA will pair with other nucleotides in the same molecule to form intrastrand bonds. For example, when a DNA sequence contains inverted repeated sequences (known as "palindromes"), hydrogen-bonded hairpin structures may form. As is well known in the art, these structures may contain "loops" of nucleotides that do not participate in the intrastrand bonding. Stem and loop structures are known to function in regulating a number of molecular genetic events by, e.g., interacting with DNA binding regulatory proteins.

While a DNA molecule may contain all the necessary information to make a given protein, DNA does not serve as a direct template for making proteins. Instead, in a process called transcription, DNA serves as a template for the synthesis of a structurally-related intermediate molecule called ribonucleic acid ("RNA"). RNA is essentially an imprint of DNA. RNA and DNA, however, differ in three major ways: (1) the sugar backbone of RNA is ribose rather than deoxyribose; (2) RNA exists as a single polymer (single stranded); and (3) the nucleotide thymidine found in DNA is replaced by the nucleotide uridine (U).

There are several subclasses of RNA molecules: messenger RNA, transfer RNA, and ribosomal RNA. Messenger RNA ("mRNA"), is responsible for delivering the information coded by the DNA in the nucleus to the cell's protein machinery in the cytoplasm. In a process called translation, cells synthesize proteins using mRNA as a template (i.e., cells "translate" the nucleic acid language into amino acid language). Three nucleotides (a "codon") within the mRNA define, or code, for a specific amino acid. The codons that code for specific amino acids are known and referred to as the genetic code.

Over the years, scientists have discovered that RNA participates in other biological processes. To perform these biological processes, single stranded RNA molecules typically fold to form secondary or tertiary structures. The secondary and tertiary structures are usually maintained by conventional Watson and Crick base pairing between nucleotides found throughout the single stranded RNA. Increasingly, however, scientists are discovering that RNA tertiary structure is often held together by non-conventional base pairing (e.g., G-U) and base triples (e.g., U-A-U).

The tertiary structure of transfer RNA (tRNA) was one of the first to be studied. Scientist have determined the nucleotide sequence of several hundred tRNA molecules isolated from numerous organisms. The tRNA molecules are all between 73 and 93 nucleotides. While the exact nucleotide sequences vary, certain nucleotides are conserved from one tRNA to another. These conserved nucleotides confer a three-dimensional L-shaped structure, which is often depicted as a two-dimensional cloverleaf-like structure. Most of the base pairs and base triples that form the tertiary structure are conventional.

Tertiary structures have also been observed for self-splicing RNA. Studies in *Tetrahymena thermophilia*, for example, reveal that intron splicing of ribosomal RNA ("rRNA") does not require proteins, but rather is intrinsic to the rRNA molecule. In an elaborate set of reactions, a 413 nucleotide intron is excised in a series of phosphoester transfer reactions. The predicted tertiary structure of the Tetrahymena rRNA brings the 5' and 3' ends of the intron into close proximity. The tertiary structure is confirmed by experiments in which small deletions in the intron remote from the splice junction completely prevent splicing.

RNA tertiary structure may also be found in the coding regions of genes. Retroviruses use translational suppression to express the pol and gag genes as one large fusion protein. The pol genes encode enzymatic proteins integrase, protease, and reverse transcriptase, while the gag genes encode structural proteins. Greater quantities of the structural gag gene products are required. To produce the enzymatic and structural proteins in different amounts, some retroviruses use ribosomal frameshifts and read-through. Thus, a single fusion protein is synthesized from two or more overlapping genes by altering the reading frame. Recently, it has been discovered that ribosomal frameshifting requires a heptanucleotide sequence that comprises the actual frameshift site, and an RNA tertiary structure downstream of the frameshift site. Specifically, the tertiary structure comprises a psuedoknot. A psuedoknot is formed when a region outside a hairpin loop base pairs with a complementary sequence on the bulge of the hairpin loop. Studies suggest that frame shifting is psuedoknot dependent.

It will be appreciated that the function and regulation of a nucleic acid frequently depends on the formation of intrastrand structures. As more nucleic acid sequence information is accumulated, the ability to detect such structures becomes increasingly important. Existing methods for identifying such structures, however, are limited. While some existing methods search for palidromic sequences and stem-loop structures, these methods do not search for permutations of such structures.

It will also be appreciated that in some cases disrupting the secondary and tertiary structure of a nucleic acid may be desirable. For example, many virus are harmful to humans and are responsible for numerous diseases. The ability to identify such structures may lead to faster development of antiviral therapies.

BRIEF SUMMARY OF THE INVENTION

From the forgoing, it will be appreciated that it would be an advancement in the art to determine portions of nucleic acid which form intrastrand bonds. It would especially be an advancement to determine which sequences form R-structures and wings.

It would be a further advantage to identify viral nucleic acid sequences that form tertiary structure. Such sequences may yield important therapeutic targets.

The present invention relates to self-hybridizing nucleic acid elements that appear to play a role in a number of molecular genetic events. More specifically, the present invention relates to methods for identifying resonating, self-hybridizing nucleic acid elements. These structures are referred to herein as R-structures. The present invention also relates to methods for identifying nucleotide sequences that can base pair with the nucleotides in an R-structure. Such structures are referred to herein as wings.

The method of the present invention has been developed in response to the present state of the art, and in particular, in response to the problems and needs in the art that have not yet been fully solved by currently available technology. Thus, the present invention provides a method for quickly and accurately identifying R-structures within nucleic acid molecules.

To achieve the foregoing, and in accordance with the invention as embodied and broadly described herein in the preferred embodiment, a method for identifying self-hybridizing sequences in DNA strands is provided. The method comprises selecting a DNA sequence of interest, determining a minimum number of base pairs necessary in potential R-structures, determining a maximum loop size necessary in a potential R-structure to be identified, identifying a first potential stem sequence within the DNA sequence, identifying a second potential stem sequence within the DNA sequence, and comparing the nucleotides in the first and second potential stem sequences to determine whether the minimum number of base pairs exist within the first and second potential stem sequences. In certain preferred embodiments, the step of comparing the nucleotides in the first and second potential stem sequences is conducted with a computer.

These and other features and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention has been developed in response to the above-discussed need in the art for a method of identifying and locating R-structures. An "R-structure" is a resonating, self-hybridizing molecular genetic nucleotide structure. The term "resonating" refers to the ability of one or more nucleotide sequences to form alternative thermodynamically stable base pairings. An R-structure is a hairpin or a stem and loop structure capable of hybridizing with "wing" sequences that may be located upstream and/or downstream of the hairpin or stem and loop structure. A wing is a sequence located elsewhere in the nucleic acid molecule which hybridizes to a hairpin or stem and loop structure and which can itself be a hairpin or stem and loop structure. R-structures can hybridize to other R-structures in a resonating manner. Without being bound by any particular theory, such structures are believed to play a role in a number of molecular genetic events.

The term "nucleic acid sequence" refers to both naturally occurring and synthetic DNA and RNA sequences. The term captures sequences that include base analogues of DNA and RNA such as, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, 2-thiocytosine, and 2,6-diaminopurine.

The method is disclosed in an embodiment for use in identifying and locating the resonating, self-hybridizing nucleic acid elements in a DNA strand, but one skilled in the art will readily understand how the method can be modified to identifying and locating R-structures in other nucleic acids, such as RNA.

Figure 1:
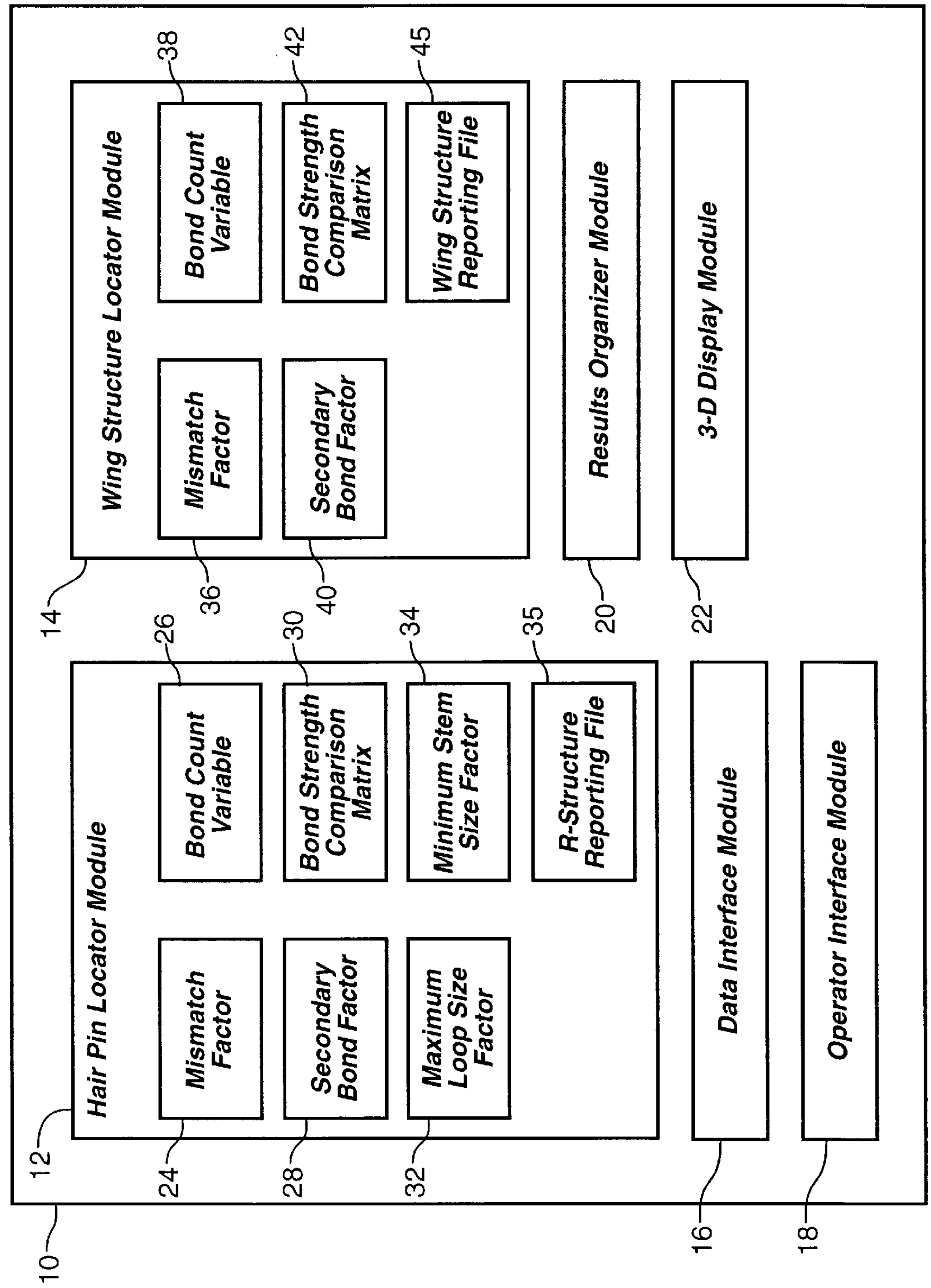
FIG. 1 is a block diagram illustrating a system of computer program elements for identifying and locating resonating, self-hybridizing nucleic acid elements.
Figure 2A:
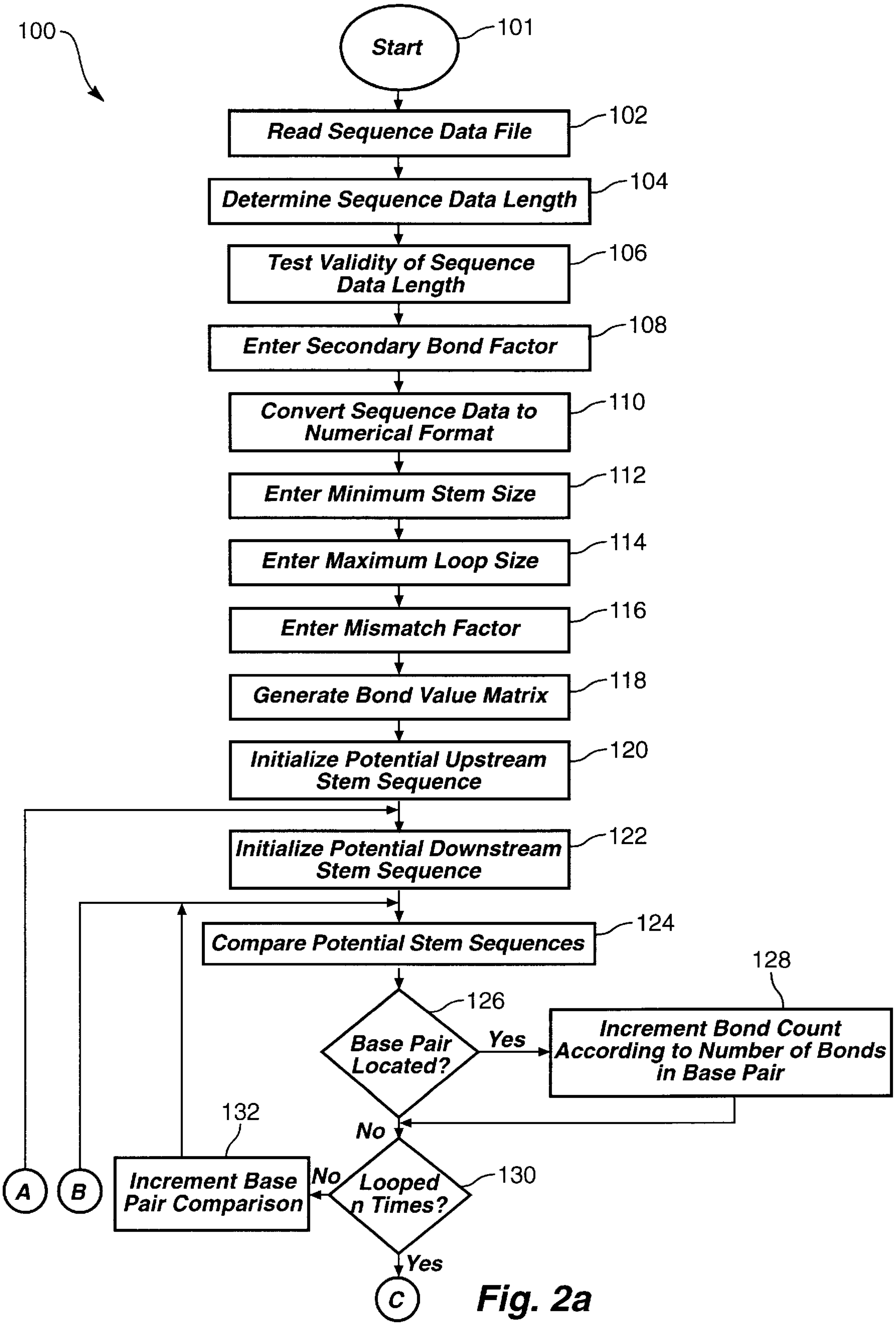
FIG. 2*a* is the first half of a flow chart diagram illustrating the various steps in a method of identifying and locating resonating, self-hybridizing nucleic acid elements.
Figure 2B:
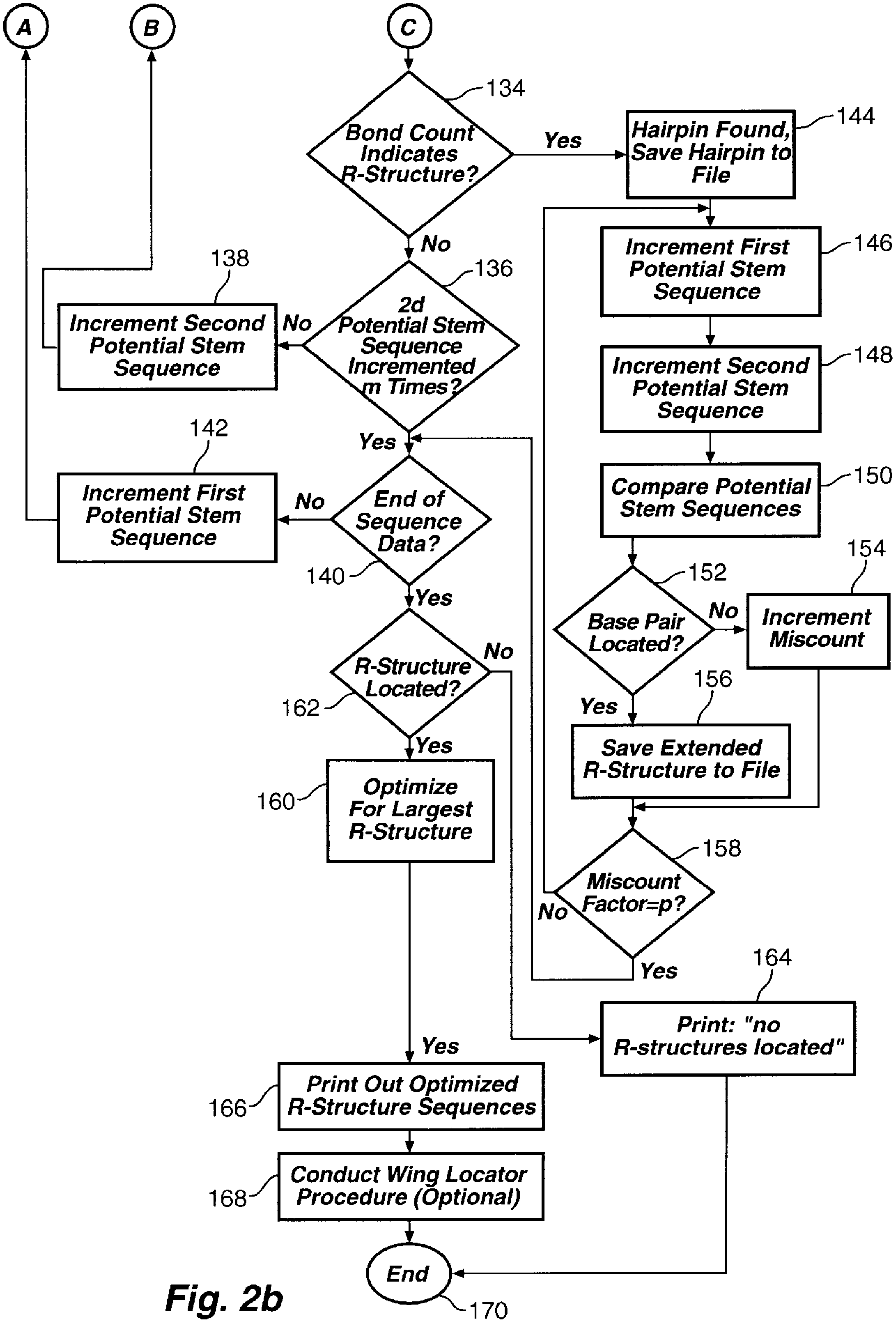
FIG. 2*b* is the second half and represents a continuation of the flow chart diagram of FIG. 2*a*.
Figure 3A:
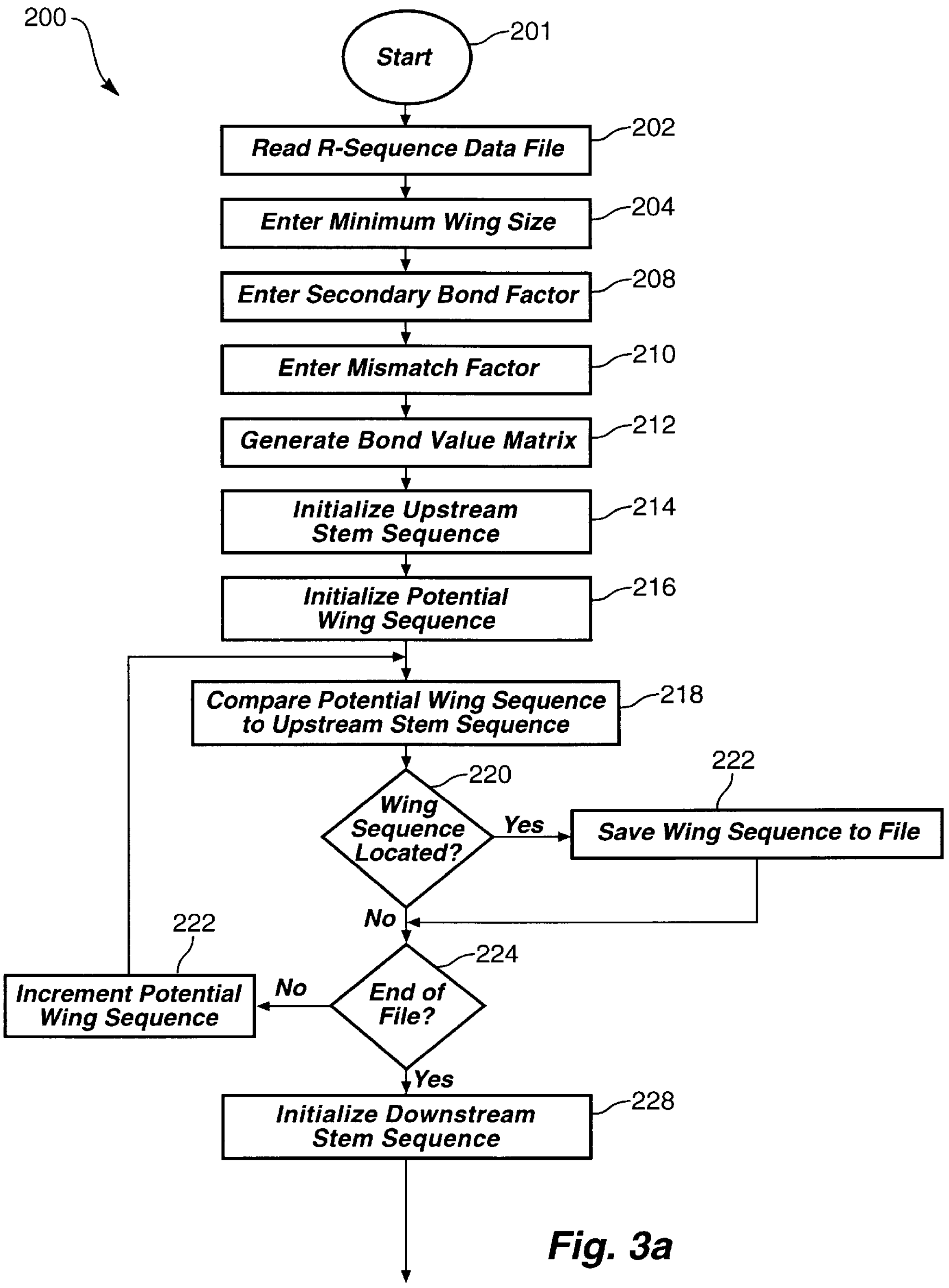
FIG. 3*a* is the first half of a flow chart diagram illustrating the various steps in a method of identifying resonating wing structures within an identified resonating, self-hybridizing nucleic acid element.
Figure 3B:
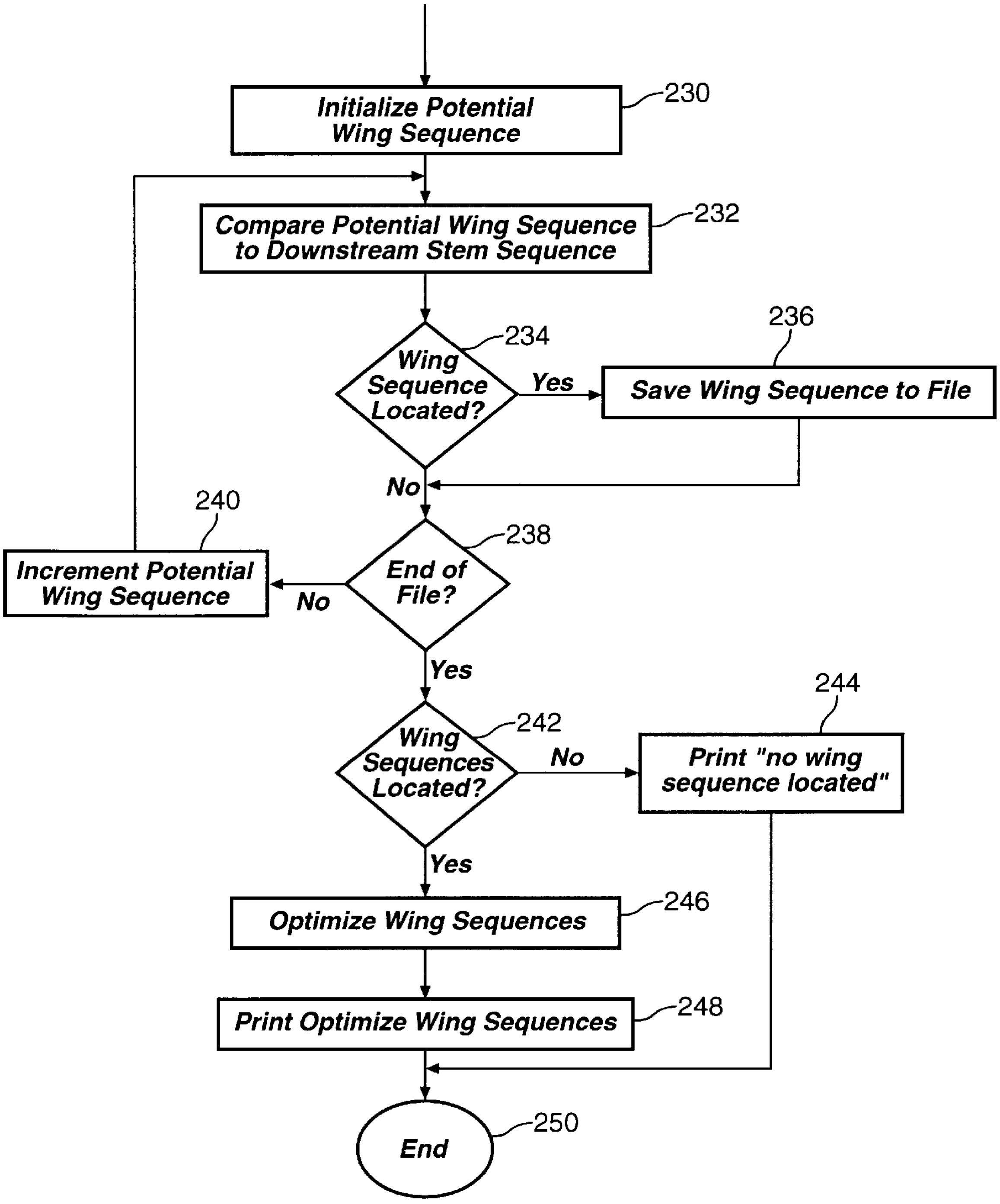
FIG. 3*b* is the second half and represents a continuation of the flow chart diagram of FIG. 3*a*.

FIGS. 1 through 3 illustrate a computer software program for automatically identifying and locating R-structures within an identified sequence of nucleic acid elements. Shown in FIG. 1 is the R-structure identifier program 10, having therein separate modules including an R-structure locator module 12, a wing structure locator module 14, a data interface module 16, a results organizer module 20, an operator interface module 18, and a 3-D display module 22.

The R-structure locator module 12 includes various data structures and data operator modules used in locating base pairs within a nucleic acid sequence, determining if groups of base pairs are of an appropriate configuration to form an R-structure, and determining the optimum size of located R-structures.

A mismatch factor block 24 within the R-structure locator module 12 allows for the occurrence of non-bonding pairs within an R-structure. In accordance with the present invention, not every set of potential base pairs needs to form a full or even a partial bond. Accordingly, using parameters consistent with specific types of R-structures to be located, an operator preferably provides a mismatch factor 24 indicative of the number of non-bonding base pairs that may exist in an R-structure sequence.

A bond count variable block 26 provides a bond count under which the number of bonds within a potential base pair are enumerated. A secondary bond factor block 28 allows an operator to indicate whether secondary bonds should be included in bond strength calculations.

A bond strength comparison matrix 30 is used to compare two nucleotides to determine if sufficient energy exists in bonds between the two nucleotides such that the two can constitute base pairs of an R-structure. In one embodiment, the bond strength comparison matrix is provided as shown in FIG. 4.

Figures 4, 5:
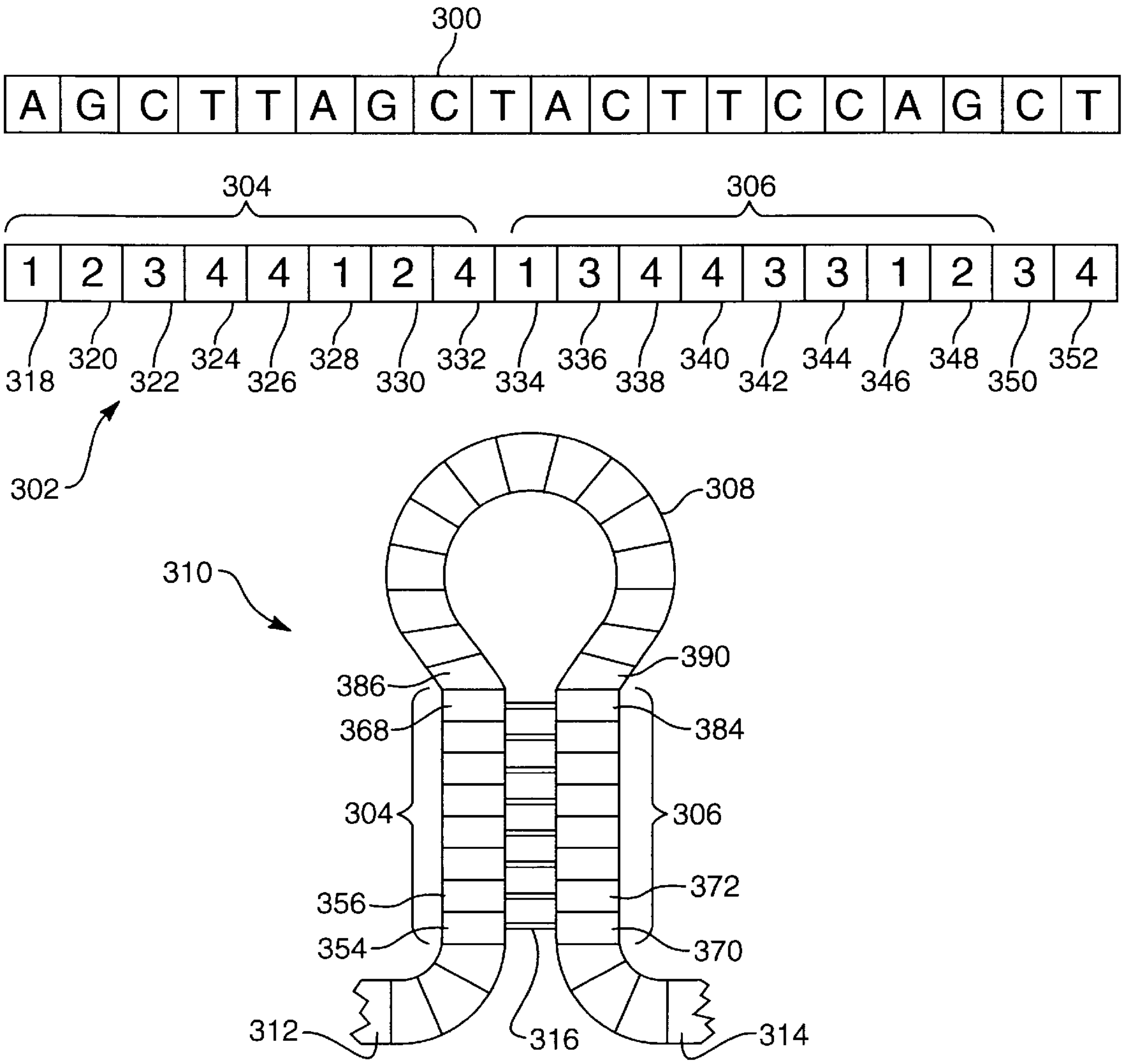
FIG. 4 is a bond strength comparison matrix.
FIG. 5 schematically illustrates a nucleic acid sequence capable of forming a stem and loop structure.

In the depicted embodiment of FIG. 4, the bond strength comparison matrix 30 lists the potential types of bases for two DNA strand segments. The bases for one segment are listed in a row across the top and the bases for the other segment are listed in a column along the left side of the matrix. The base types, A, G, C, and T, are also translated into the integers 1, 2, 3, and 4 respectively. A bond factor, which is indicative of the strength of the bond between two nucleotides, is given at the intersection between the two respective types of bases. It will be appreciated that in other embodiments, a bond strength comparison matrix could be constructed that included base analogues.

The R-structure locator module 12 uses the matrix 30 to calculate the strength of a potential bond between two potential R-structure candidates and then compares that energy to an optimum desired value. Weaker bonds can be considered or deleted from any comparison using the matrix. Of course, a look-up table or other suitable data construct could be used in place of the bond strength comparison matrix 30 to indicate the number of potential bonds between two nucleotides or the energy created by the potential bonds.

The maximum loop size factor block 32 is a data structure for storing a user input value representing the maximum number of non-bonded nucleotides that may exist within a candidate R-structure.

A minimum stem size factor 34 is similarly a data structure storing a user input value representing a minimum number of base pairs in a stem sequence of a candidate R-structure. An R-structure reporting file 35 is used to store the located potential R-structures during operation of the R-structure locator module 12.

Within the wing structure locator module 14 of FIG. 1 is found a mismatch factor 36, a bond count variable 38, a secondary bond factor 40, and a bond strength comparison matrix 42. These modules and data structures perform similar functions to their counterparts in the R-structure locator module 12.

A wing structure reporting file 45 is used to store the located potential wing structures.

The data interface module 16 of the R-structure identifier program IO of FIG. 1 is preferably used to input strings of DNA sequences from a data file and also to output those strings of sequences to a data file or to a printer.

The operator interface module 18 provides an interface by which the operator may control the program and select the various operator-input factors discussed above. Preferably, the operator interface module 18 is presented with a menu structure or some other user-friendly manner.

The results organizer module 20 is used to organize the results of the R-structure search and the wing structure search, selecting from among cumulative sequences the most optimal sequence. For example, where different sets of located potential R-structures are cumulative, but one is longer than the others, the results organizer module 20 may be configured to select the longer R-structure. A similar criterion may be used to select the optimal wing structure in a set of cumulative or otherwise redundant located wing structures.

A 3-D display module 22 may also be included within the R-structure identifier program 10. In one embodiment, the 3-D display module 22 is used to display the located R-structures with a 3-D visual presentation on a computer screen or on a printout.

Referring now to FIGS. 2*a* and 2*b*, shown therein is a flow chart diagram illustrating one manner of operation of a method 100 of locating R-structures within a nucleotide sequence. The method 100 may be conducted using a software program, and in the depicted embodiment most or all of the steps of the method 100 are carried out by the R-structure identifier program 10 of FIG. 1. Various illustrative steps of the method 100 are represented by numbered blocks in the flow chart diagram of FIGS. 2*a* and 2*b*.

The method 100 starts at a block 101 and proceeds on to a read sequence data file step 102. The sequence data file read in at the read sequence data file step of block 102 is alphanumeric representation of the base types of nucleotides in a DNA sequence. For example, the sequence data file may contain a sequence of the letters A, G, C, and T, representative of DNA nucleotides. Such an embodiment is represented at 300 in FIG. 5. Of course, when representing RNA sequences or sequences containing base analogues, appropriate adjustments must be made.

Upon reading in the sequence data files, the method 100 proceeds to a step indicated by a block 104, where the length of the DNA sequence data in the sequence data file is determined. Thereafter, at a block 106, the validity of the sequence data length is tested. Thus, if the sequence is too short to form an R-structure, or if it is above a predetermined length, an error report may be generated. At this point, the data may also be tested to ensure that the data is of the proper type. At a subsequent block 108, a secondary bond factor as discussed above is entered by a user and stored within the secondary bond factor data construct 28. The secondary bond factor is typically entered as a “1” or a “0,” indicating whether or not G-T base pairing should be included in the base pairs of a potential R-structure.

The method 100 progresses to a block 110, where the sequence data file is converted to a numerical format. In one embodiment, this comprises converting each “A” to a “1,” each “G” to a “2,” each “C” to a “3,” and each “T” to a “4.” Of course, any combination of numbers could be used, and the letters could also be compared to each other as letters. At a block 112, a minimum desired stem size is entered. In one embodiment, the minimum stem size default is 8, but other minimum stem sizes for forming an appropriate R-structure could also be entered at this point. At a block 114, the user is prompted to enter the maximum loop size. In one embodiment, the maximum loop size default is 20.

At a block 116*a* user is prompted to enter a mismatch factor which provides an allowance for weak bond pair matching or non-bond pair matching bases. At a block 118, a bond value matrix, as described above, is generated logically by the computer software.

At a block 120, potential upstream stem sequence is initialized. Referring now to FIG. 5, one potential upstream sequence is referenced, at number 304 of a DNA strand 302. Typically, the first upstream stem sequence will be at one end in the depicted figures at the left hand side of the DNA strand.

At a block 122, a potential downstream stem sequence, referenced at 306 in FIG. 5, is initialized. Initially, the potential downstream stem sequence 306 will be the sequence of nucleotides directly 3' to the nucleotides of the upstream stem sequence. The upstream and downstream stem sequences initially have a length corresponding to the minimum stem size factor 34 entered by the operator. Since there will always be a certain frequency of random base pairings possible between any two sequences, the minimum stem size factor 34, which is represented by n, may be chosen to reduce noise.

Referring now to block 124, the potential stem sides 304, 306 are compared. This comparison is preferably done as a loop, comparing corresponding possible bases for potential bonding capabilities. Thus, for strand 302 of FIG. 5, the base numbered 318 would initially be compared with the base numbered 348. In the method 100, this is conducted at block 126. Thus, the program loops through, as shown at block 130, n times. The second comparison would compare block 320 with block 346, the third comparison would compare block 322 with block 344, etc., n times. After each comparison, the program increments the base pair being compared at block 132. Once the minimum number of potential base pairs have been compared, the answer to the query at block 130 is "yes" and the method 100 moves on to block 134.

For each base pair that is queried at block 126, a bond count is incremented at block 128. The bond count preferably represents the number of bonds in each base pair and determination is made using the matrix of FIG. 4. Thus, once the minimum stem size has been examined, potential stem sequences can be determined to be an R-structure or not as conducted at block 134.

The bond count variable 26 of FIG. 1, which was updated at block 128 of FIG. 2*a*, is compared to the mismatch factor 24 which was generated according to the amount of energy required for an R-structure to self-hybridize and thereby form. If this comparison is favorable, the answer to the query at block 134 is "yes" and the program moves to block 144, where the program registers that a hairpin has been found, and the hairpin is saved to a file.

If a sufficient number of bonds is not located, the answer to the query at block 134 is "no" and the program moves to block 136. The query at block 136 asks whether the second potential stem sequence has been incremented m times. The first time, m will be "0," after which the program will move to block 138, incrementing the second potential stem sequence such that the next time through m is "1." This will continue until m reaches the maximum loop size set at block 114, for which the default is, as discussed, 20.

At block 138, the second potential stem sequence, shown at 306 in FIG. 5 is incremented. Thus, the sequence is incremented to eliminate the first nucleotide in the sequence and to include the subsequent nucleotide previously not included in the sequence. The program then loops up to block 124 where the potential stem sequences are once again compared. This process continues, as discussed above, determining whether the potential stem sequence 304 matches with any second potential stem sequences, extending from the nucleotide 334 of the DNA sequence 302, until a nucleotide to any location beyond the nucleotide 348, which is not shown.

At this point, to compare further would extend beyond the natural loop size, which is not allowed by the program. Accordingly, the program moves to block 140, where it asks if the first potential stem size is n locations from the end of the sequence file. If not, at 142, the first potential stem sequence is incremented. Thus, in FIG. 5, the DNA strand 302 would be incremented to dis-include location 318 and to subsequently include location 334. The program loops to block 122, at which point a potential downstream stem sequence, including blocks 336 through 350, is initialized. The program then continues looping as discussed above, until the answer to the query of block 140 is known. At this point, each potential stem sequence will have been compared with every other potential matching stem sequence to determine whether R-structures exist.

Digressing momentarily to block 144, in each case where a hairpin is found and has been saved to a file, the program then moves to block 146. At block 146, the program initiates a procedure whereby it tests to find whether the R-structure as now found may have more than the minimum size. Thus, the first potential stem sequence is incremented to include, in addition to the previous eight or whatever the minimum stem size amount of locations were, the next subsequent location. Thus, in the example given, the first potential upstream stem sequence 304 would, in addition to locations 318–332, also contain location 334.

Subsequently, at block 148, the second potential stem sequence is also incremented to include the next location which, as can be seen from the sequence 310 of FIG. 5, is actually the preceding location which would be location 390 of the sequence 310 of FIG. 5.

At block 150, the two above-discussed potential stem sequences are compared to determine if sufficient base pairing exists. Thus, at a block 152, the program queries whether a base pair is located. The existence of a base pair is once again determined with the matrix of FIG. 4, to determine if sufficient energy exists. If the base pair does exist, the program moves to block 156. If the base pair does not exist, the program proceeds to block 154 where a miscount is incremented.

At block 156, in a "yes" answer to the query of block 152, the extended R-structure, including the subsequent base pair, is saved to a file. Thereafter, both branches coming from block 154 and block 156 progress on to block 158, which contains a query wherein the program checks to see whether the miscount variable at block 154 corresponds to a maximum number of non-bonded pairs, indicated by p. This miscount variable factor is typically entered by the operator in advance of the program, and comprises the number of non-bonding corresponding bases that may exist in an extended R-structure. If the miscount factor has not been exceeded, the program loops back up to FIG. 146 to examine the subsequent potential stem sequences to determine whether the R-structure can be extended. If the answer to the query at block 158 is "yes," the program returns to block 140 of the program.

When the answer to the query of block 140 is "yes," the program proceeds to block 162, which checks the files to which any located R-structures or extended R-structure were to be written. If the file contains R-structures, the answer to the query of block 162 is "yes" and the program proceeds to block 160. At block 160, the contents of the files are searched and organized using the results organizer module 20 of FIG. 1 to select the largest, optimum R-structure. Those optimized R-structures are then printed at block 166. Additionally, the wing locator procedure which will be discussed below may also optionally be conducted at this point. Programming ends at block 170. If the answer to the query at block 162 is "no," the program prints "no R-structures located."

The present invention also contemplates a wing structure locator program. FIG. 3*a* depicts one embodiment of a wing structure locator program diagram. As shown therein, the program starts at a block 200 and thereafter proceeds to a block 202. At the block 202, an R-structure sequence data file is read in. The R-structure sequence data file may be entered by an operator, or may be output file from the R-structure locator program 12 of FIG. 1, as discussed previously.

At a block 204, the program prompts the operator for a minimum wing size to be searched. In one embodiment, the minimum wing size is six nucleotides.

At a block 210, a mismatch factor is entered that determines the number of non-bonds that may exist between the upstream stem sequence and counterpart wing sequence. At a block 208, a secondary bond factor is entered, as discussed above, to determine whether G-T bonds will be counted as suitable, R-structure-forming bonding structures. At a block 212, the bond value matrix discussed above and shown in FIG. 4, or an equivalent thereof, is generated.

At a block 214, an upstream stem sequence is initialized. The upstream stem sequence is typically the beginning of the DNA sequence, such as sequence 304 in FIG. 5, and as discussed above.

At a block 216, a potential wing sequence is initialized. The potential wing sequence may be similar to sequence 306 of FIG. 5, but being of a length entered at block 204.

At a block 218, the potential wing sequence is compared to the upstream stem sequence to determine if sufficient energy exists for the two to form a self-hybridizing wing structure.

In this process at block 220, the program checks whether the wing sequence has been located. This is typically conducted in the same manner as discussed above at blocks 126, 130, 132, and 124. This includes incrementing through the potential wing sequence, comparing it to the counterpart bases in the upstream stem sequence. If a wing sequence is located, the program proceeds to block 222, where the wing sequence is saved to a file. At block 224, the program checks whether the DNA sequence has been tested all the way to the end of the file. If not, the potential wing sequence is incremented such that if the wing sequence were segment 306 of FIG. 5, the segment would then be incremented to disinclude base 334 and to subsequently include base 350.

The program then moves back to block 218, where the new wing sequence is tested for sufficient bonds to form a wing sequence with the upstream stem sequence. If the answer to the query at block 224 is "yes," the program proceeds to block 228, wherein the downstream stem sequence is initiaed. Thus, using the sequence of FIG. 5 as an example, if in the R-structure locator module program 12 discussed above, two potential stem sequences were found, an upstream stem sequence 304 and a downstream stem sequence 306, the upstream stem sequence would be sequence 304 and the downstream stem sequence would be sequence 306. The program would then initialize a potential wing sequence, which could be referring to sequence 302, it could be within the sequence 304, or 5' to the sequence 304, or 3' to the sequence 306. It could also include the looping sequence between the two DNA structures, referred to in the sequence 310 as locations 386–390, also referred to as the loop structure 308.

Thereafter, at a block 230, the potential wing sequence is initialized. At a block 232, the potential wing sequence is compared to its counterpart downstream stem sequence to determine if sufficient bonds exist to create base pairs sufficient to form a wing sequence.

In making this comparison at block 234, the program checks to see if a wing sequence is located. This is similar to the procedure at block 220. If the answer is "yes" the wing sequence is saved to a file at block 236; if the answer is "no" the program proceeds to block 238, or it again checks to see if it is at the end of the file. If it is not at the end of the file, the program continues to loop, passing through block 240, wherein the potential wing sequence is incremented, and back to block 232.

If the end of the file has been reached, the program checks to see if any wing sequences were located and written to the file 45. If no wing sequences were located, the program at block 244 prints "no sequences located." If wing sequences were located, at block 246, the program then optimies the wing sequences using the results organizer module 20 of FIG. 1, then prints those optimized link sequences at block 248. The program then terminates at block 250.

EXAMPLES

The following example is given to illustrate one embodiment which has been made with the present invention. It is to be understood that the following example is not comprehensive or exhaustive of the many types of embodiments which can be prepared in accordance with the present invention.

Example 1

R-Structures in the Ebola Virus Nucleic Acid Sequence

In one embodiment, the nucleic acid folding prediction program was run on the Ebola virus nucleic acid sequence. The Ebola virus is an enveloped, filamentous virus containing an RNA genome of the nonmessage sense. The Ebola genome comprises 11740 nucleotides. A. Sanchez et al. (1989), *Virology* 170, 81–91, incorporated herein by reference; A. Sanchez et al. (1993), *Virus Res.* 29, 215–240, incorporated herein by reference. The genomic organization and transcriptional signals of Ebola are homologous to those of other nonsegmented, negative-strand RNA viruses, especially to members of the Paramyxovirus and Morbillivirus genera of viruses.

When applied to the DNA sequence corresponding to the RNA sequence of the Ebola virus genome, the computer program of the present invention reveals at least two types of tertiary structures which are herein referred to as R-structures and wings. Below, the tertiary structure, interaction and location of R-structures and wings is discussed in greater detail.

R-Structures. The RNA folding program revealed at least ten regions in the Ebola genome that potentially form resonating, self-hybridizing nucleic acid elements or tertiary structures. These regions are herein referred to as R-structures. The nucleic acid regions range from 21 to 74 nucleotides. These R-structures are designated with an asterisk (*) followed by the number of the first nucleotide of the R-structure followed by another asterisk (*); e.g., "5*" designates an R-structure beginning at nucleotide number 5 of the Ebola genome. Table I lists ten R-structures found in the Ebola genome.

TABLE I

| R-structure | Nucleotides | Nucleotide Sequence | |
|---|---|---|---|
| *5* | 5–44 | CACACAAAAAGAAAGAAGAATTTTTAGGATCTTTTGTGTG | (SEQ ID NO: 1) |
| *56* | 56–113 | GAGGAAGATTAATAATTTTCCTCTCATTGAAATTTATATCGGAAT-TTAAATTGAAATT | (SEQ ID NO: 2) |
| *3029* | 3029–3061 | TAATGATGAAGATTAAAACCTTCATCATCCTTA | (SEQ ID NO: 3) |
| *4402* | 4402–4435 | GAAAAACCTACCTCGGCTGAGAGAGTGTTTTTTC | (SEQ ID NO: 4) |
| *5599* | 5899–5939 | GCGATGAAGATTAAGCCGACAGTGAGCGTAATCTTCATCTC | (SEQ ID NO: 5) |
| *6067* | 6067–6087 | CCTCGTGATCGATTCAAGAGG | (SEQ ID NO: 6) |
| *6097* | 6097–6128 | TTTCTTTGGGTAATTATCCTTTTCCAAAGAAC | (SEQ ID NO: 7) |
| *8255* | 8255–8328 | ATCAATCTAGTTATCTCTTTGAGAATGATAAACTTGATGAAGAT-TAAGAAAAAGGTAATCTTTCGATTATCTTT | (SEQ ID NO: 8) |
| *9719* | 9719–9766 | TCTCTTAAAATATTAAGAAAAACTGACGGAACATAAATTCTTTA-TGCT | (SEQ ID NO: 9) |
| *9787* | 9787–9845 | TTGGTATTGGCTATTGTTATATTACAATCAATAACAAGCTTGTAAA AATATTGTTCTTG | (SEQ ID NO: 10) |

The R-structures shown in Table I can form a variety of tertiary structures, from simple hairpin loops to more complex structures. As illustrated below, R-structure *5* can form a hairpin loop having 14 Watson-Crick base pairs.

```
      5
5' - C A C A C A A A A A G A A A G A A G A A
     | | | | | | | | |       | | | |
3" - G T G T G T T T T C T A G G A T T T T T
      44
```

As illustrated below, R-structure *56* can form several hairpin loops stabilized by numerous base pairs.

```
      56
5' - G A G G A A G A T T A
     | | | | | | | | | | |A
     C T C C T T T T A A T
     78

      67
5' - A T A A T T T T C C T C T
     | | | |   | | | |
3' - T A T T T A A A G T T A C
     92

      81
5' - A T T G A A A T T T A T A
     | | |   | | | | | |
3' - T A A A T T T A A G G C T
     106

      81
5' - A T T G A A A T T T A T A T C G
                 | | | | |
           3' - T A A A T T T A A G
                 106

      86
5' - A A T T T A T A T C G
     | | | | | | |   | |
3' - T T A A A T T T A A G
     107
```

-continued

```
      98
5' - A A T T T A A A
     | | | | |   |
3' - T T A A A G T T
      113
```

In addition to the various hairpin loops that can be formed by the nucleotides residing in the R-structure, as illustrated in FIG. 1, R-structure *56* can form a complex tertiary structure stabilized by 38 base pairs.

As illustrated below, R-structure *3029* can form several hairpin loops stabilized by numerous base pairs.

```
      3029
5' - T A A T G A T G A A G A T T A A
     | | |   | | | | |   | |         A
3' - A T T C C T A C T A C T T C C A
      3061

           3029
     5' - T A A T G A T G A A G A T T A
          | | | | | | | | |   | |
3' - A T T C C T A C T A C T T C C A A A
      3061
```

As illustrated below, R-structure *5899* can form several hairpin loops stabilized by numerous base pairs.

```
      5899
5' - G C G A T G A A G A T T A A G C C G A C
       |   | | | | | | | | | | |   | |   |   A
3' - C T C T A C T T C T A A T G C G A G T G
      5939

      5899
5' - G C A T G A A G A T T A A G C C G A C A G T
                 | | | |   | | |       | |   | G
           3' - C T C T A C T T C T A A T G C G A
                 5939
```

As illustrated below, R-structure *8255* can form several hairpin loops stabilized by numerous base pairs.

```
    8255
5'-ATCAATCTAGTTAT
    ||||  |||        C
3'-TAGTAAGAGTTTCT
    8283
```

```
    8255
5'-ATCAATCTAGTTATCTCTTT G
           |||  ||||
       3'-TAGTTCAAATAGTAAG A
           8283
```

```
    8293
5'-GAAGATTAAGAA
    ||||||||       A
3'-TTTCTAATGGAA
    8317
```

```
    8293
5'-GAAGATTAAGAAAAAGGTAATCT
T
                  |||||||||
             3'-TTTCTATTAGC
T
                  8328
```

In addition to the various hairpin loops shown above, R-structure *8255* can form a complex tertiary structure stabilized by 19 base pairs.

As illustrated below, R-structure *9719* can form several hairpin loops stabilized by numerous base pairs.

```
    9719
5'-TCTCTTAAAA
    |  ||||||  |
3'-AAAGAATTAT
    9738
```

```
    9729
5'-TATTAAGAAAAACTGAC G
    |||  |||||      ||
3'-GTATTTCTTAAATACAA G
    9764
```

```
    9748
5'-AACATAAAT
    |  ||||||   T
3'-TCGTATTTC
    9766
```

In addition to the various hairpin loops that can be formed, R-structure *9719* can form a complex tertiary structure stabilized by 24 base pairs.

Wings. The nucleic acid folding program revealed numerous remote regions in the Ebola genome that potentially hybridize to the R-structures described above. These regions are herein referred to as wings. The wings themselves may reside within the R-structures. Thus, for example, the sequence $^{9}$CAAAAAGAA found within R-structure *5* can hybridize to the sequence $^{9756}$TTCTTTATG found within R-structure *9719*. A number of wing nucleic acid sequences and the sequences they base pair with are shown below in Table II.

TABLE II

<table>
<tr><th>R-Structure</th><th>Wing Sequence</th><th>R-Structure</th><th>Wing Sequence</th><th>Base Pairing</th></tr>
<tr><td>*5*</td><td>$^{9}$CAAAAAGAA</td><td>*9719*</td><td>$^{9756}$TTCTTTATG</td><td>CAAAAAGAA<br>|| ||||||<br>GTATTTCTT</td></tr>
<tr><td></td><td>$^{20}$AAGAATTTTT<br>(SEQ ID NO: 11)</td><td>*9719*</td><td>$^{9751}$ATAAATTCTT<br>(SEQ ID NO: 12)</td><td>AAGAATTTTT<br>|||||||| |<br>TTCTTAAATA</td></tr>
<tr><td>*56*</td><td>$^{54}$ATGAGGAAG</td><td>*3029*</td><td>$^{3048}$CTTCATCAT</td><td>ATGAGGAAG<br>|||| |||<br>TACTACTTA</td></tr>
<tr><td></td><td>$^{56}$GAGGAAGATTA<br>(SEQ ID NO: 13)</td><td>*5899*</td><td>$^{5927}$TAATCTTCATC<br>(SEQ ID NO: 14)</td><td>GAGGAAGATTA<br>|| ||||||||<br>CTACTTCTAAT</td></tr>
<tr><td></td><td>$^{56}$GAGGAAGATTAA<br>(SEQ ID NO: 15)</td><td>*8255*</td><td>$^{8327}$TTAATCTTCATC<br>(SEQ ID NO: 16)</td><td>GAGGAAGATTAA<br>|| |||||||||<br>CTACTTCTAATT</td></tr>
<tr><td></td><td>$^{86}$AATTTATAT</td><td>*9719*</td><td>$^{9749}$ACATAAATT</td><td>AATTTATAT<br>||||||| |<br>TTAAATACA</td></tr>
<tr><td></td><td>$^{64}$TTAATAATTT<br>(SEQ ID NO: 17)</td><td>*9719*</td><td>$^{9725}$AAAATATTAA<br>(SEQ ID NO: 18)</td><td>TTAATAATTT<br>|||||| |||<br>AATTATAAAA</td></tr>
<tr><td>*3029*</td><td>$^{3048}$CTTCATCAT</td><td>*56*</td><td>$^{54}$ATGAGGAAG</td><td>CTTCATCAT<br>|||| ||||<br>GAAGGAGTA</td></tr>
<tr><td></td><td>$^{3033}$GATGAAGATTA<br>(SEQ ID NO: 19)</td><td>*5899*</td><td>$^{5927}$TAATCTTCATC<br>(SEQ ID NO: 20)</td><td>GATGAAGATTA<br>|||||||||||<br>CTACTTCTAAT</td></tr>
</table>

TABLE II-continued

<table>
<tr><th>R-<br>Structure</th><th>Wing<br>Sequence</th><th>R-<br>Structure</th><th>Wing<br>Sequence</th><th>Base Pairing</th></tr>
<tr><td></td><td>$^{3045}$AACCTTCATC<br>(SEQ ID NO: 21)</td><td>*5899*</td><td>$^{5901}$GATGAAGATT<br>(SEQ ID NO: 22)</td><td>AACCTTCATC<br>|| |||||||<br>TTAGAAGTAG</td></tr>
<tr><td></td><td>$^{3033}$GATGAAGATTAAA<br>(SEQ ID NO: 23)</td><td>*8255*</td><td>$^{8325}$TTTAATCTTCATC<br>(SEQ ID NO: 24)</td><td>GATGAAGATTAAA<br>|||||||||||||<br>CTACTTCTAATTT</td></tr>
<tr><td></td><td>$^{3045}$AACCTTCATCA<br>(SEQ ID NO: 25)</td><td>*8255*</td><td>$^{8289}$TGATGAAGATT<br>(SEQ ID NO: 26)</td><td>AACCTTCATCA<br>|| ||||||||<br>TTAGAAGTAGT</td></tr>
<tr><td>*5899*</td><td>$^{5927}$TAATCTTCATC<br>(SEQ ID NO: 14)</td><td>*56*</td><td>$^{56}$GAGGAAGATTA<br>(SEQ ID NO: 13)</td><td>TAATCTTCATC<br>|||||||| ||<br>ATTAGAAGGAG</td></tr>
<tr><td></td><td>$^{5927}$TAATCTTCATC<br>(SEQ ID NO: 20)</td><td>*3029*</td><td>$^{3033}$GATGAAGATTA<br>(SEQ ID NO: 19)</td><td>TAATCTTCATC<br>|||||||||||<br>ATTAGAAGTAG</td></tr>
<tr><td></td><td>$^{5926}$GTAATCTTCATC<br>(SEQ ID NO: 27)</td><td>*8255*</td><td>$^{8290}$GATGAAGATTAA<br>(SEQ ID NO: 28)</td><td>GTAATCTTCATC<br> |||||||||||<br>AATTAGAAGTAG</td></tr>
<tr><td></td><td>$^{5901}$GATGAAGATTAAG<br>(SEQ ID NO: 29)</td><td>*8255*</td><td>$^{8326}$TTTAATCTTCATC<br>(SEQ ID NO: 30)</td><td>GATGAAGATTAAG<br>||||||||||||<br>CTACTTCTAATTT</td></tr>
<tr><td>*8255*</td><td>$^{8327}$TTAATCTTCATC<br>(SEQ ID NO: 16)</td><td>*56*</td><td>$^{56}$GAGGAAGATTAA<br>(SEQ ID NO: 15)</td><td>TTAATCTTCATC<br>||||||||| ||<br>AATTAGAAGGAG</td></tr>
<tr><td></td><td>$^{8325}$TTTAATCTTCATC<br>(SEQ ID NO: 24)</td><td>*3029*</td><td>$^{3033}$GATGAAGATTAAA<br>(SEQ ID NO: 23)</td><td>TTTAATCTTCATC<br>|||||||||||||<br>AAATTAGAAGTAG</td></tr>
<tr><td></td><td>$^{8289}$TGATGAAGATT<br>(SEQ ID NO: 26)</td><td>*3029*</td><td>$^{3045}$AACCTTCATCA<br>(SEQ ID NO: 25)</td><td>TGATGAAGATT<br>|||||||| ||<br>ACTACTTCCAA</td></tr>
<tr><td></td><td>$^{8290}$GATGAAGATTAA<br>(SEQ ID NO: 28)</td><td>*5899*</td><td>$^{5926}$GTAATCTTCATC<br>(SEQ ID NO: 27)</td><td>GATGAAGATTAA<br>|||||||||||<br>CTACTTCTAATG</td></tr>
<tr><td></td><td>$^{8326}$TTTAATCTTCATC<br>(SEQ ID NO: 30)</td><td>*5899*</td><td>$^{5901}$GATGAAGATTAAG<br>(SEQ ID NO: 29)</td><td>TTTAATCTTCATC<br> ||||||||||||<br>GAATTAGAAGTAG</td></tr>
<tr><td>*9719*</td><td>$^{9758}$TTCTTTATG</td><td>*5*</td><td>$^{9}$CAAAAAGAA</td><td>TTCTTTATG<br>|||||| ||<br>AAGAAAAAC</td></tr>
<tr><td></td><td>$^{9751}$ATAAATTCTT<br>(SEQ ID NO: 12)</td><td>*5*</td><td>$^{20}$AAGAATTTTT<br>(SEQ ID NO: 11)</td><td>ATAAATTCTT<br>| ||||||||<br>TTTTTAAGAA</td></tr>
<tr><td></td><td>$^{9749}$ACATAAATT</td><td>*56*</td><td>$^{86}$AATTTATAT</td><td>ACATAAATT<br>| |||||||<br>TATATTTAA</td></tr>
<tr><td></td><td>$^{9725}$AAAATATTAA<br>(SEQ ID NO: 18)</td><td>*56*</td><td>$^{64}$TTAATAATTT<br>(SEQ ID NO: 17)</td><td>AAAATATTAA<br>||| ||||||<br>TTTAATAATT</td></tr>
</table>

Wings need not be located within R-structures. For example, the nucleotides $^{3054}$CATCCTTAinR-structure *3029* can base pair with a wing at nucleotides 9881–9888:

```
3054
C A T C C T T A
| | | |   | | |
G T A G T A A T
            9881
```

Likewise, the nucleotides $^{5928}$AATCTTCATC (SEQ ID NO: 31) in R-structure *5899* can base pair with a wing having the sequence $^{11499}$GAGGAAGATT (SEQ ID NO: 32):

```
5928
A A T C T T C A T C
| | | | | | |   | |
T T A G A A G G A G
         11499
```

The nucleotides $^{6116}$TTTTCCAAA in R-structure *6097* can base pair with a wing at nucleotides 11484–11492:

```
6116
T T T T C C A A A
| | | | |     | |
A A A A G A A T T
            11484
```

The nucleotides $^{8311}$AATCTTTC in R-structure *8255* can base pair with a wing at nucleotides 11501–11508:

```
8311
A A T C T T T C
| | | | | | | |
T T A G A A G G
          11501
```

If R-structures and wings were random occurrences with no biological significance, one would expect the structures to be found randomly throughout the Ebola genome. As illustrated in Table III, the R-structures and wings do not occur randomly. The structures are located at gene boundaries, suggesting that such structures may have important regulatory roles.

TABLE III

| | Gene Boundaries | | | |
|---|---|---|---|---|
| Gene | Transcription Start Site | Translational Stop/Poly A Site | R-Structure Locations | |
| Nucleoprotein | 54–67 | 3016–3027 | *5* | 5–44 |
| | | | *56* | 56–113 |
| vp35 | 3031–3044 | 4397–4407 | *3029* | 3029–3061 |
| vp40 | 4388–4401 | 5884–5895 | *4402* | 4402–4435 |
| glycoprotein | 5899–5912 | 8297–8307 | *5899* | 5899–5939 |
| | | | *6067* | 6067–6087 |
| | | | *6097* | 6097–6198 |
| vp30 | 8290–8301 | 9730–9740 | *8255* | 8255–8328 |

TABLE III-continued

| | Gene Boundaries | | | |
|---|---|---|---|---|
| Gene | Transcription Start Site | Translational Stop/Poly A Site | R-Structure Locations | |
| vp24 | 9883–9896 | 11483–11494 | *9719* | 9719–9766 |
| | | 11506–11516 | *9787* | 9787–9845 |
| polymerase | 11499–11510 | N/A | N/A | |

R-structures frequently occur near the transcription start site of the Ebola genes. In almost every case—*6067* and *6097* are the only exceptions—the R-structures are 5' of the initiator methionine of the gene. For example, R-structure *5* lies upstream of the nucleoprotein transcription start site. R-structure *56* partially overlaps the nucleoprotein transcription start site. R-structure *3029* overlaps the transcription start site of the vp35 protein. R-structure *4402* lies immediately downstream of the vp40 transcription start site. R-structure *5899* overlaps the transcription start site of the glycoprotein gene, while the R-structures *6067* and *6097* lie just downstream. R-structure *8255* lies immediately upstream of the transcription start site of the vp30 protein. R-structures *9719*and *9787* occur immediately upstream of the vp24 transcription start site.

Wings also lie near transcription start sites. For example, the wing at nucleotides 9881–9888 lies between the vp30 gene transcription stop/polyadenylation site and the vp24 gene transcription start site. Likewise, the wings at nucleotides 11484–11492, 11499–11508, and 11501–11508 lie immediately upstream of or overlap the polymerase gene transcription start site at nucleotides 11499–11510.

From the foregoing, it is clear that the R-structures and wings in the Ebola genome generally lie in or near transcription start sites. These data suggest that such structures may have important regulatory functions. A method of identifying such structures may facilitate understanding of the organization and regulation of nucleic acid sequences. Such structures may also provide important targets for the development of antiviral therapies. For example, antisense therapies could be developed to inhibit the formation of such structures or to interfere with the interactions of such structures with regulatory proteins.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for identifying R-structures in a nucleic acid sequence, the method comprising:

a. obtaining a nucleic acid sequence comprising a plurality of nucleotides;

b. selecting a minimum number of base pairs in an R-structure to be identified;

c. selecting a maximum loop size of an R-structure to be identified;

d. identifying a first potential stem sequence within the nucleic acid sequence;

e. identifying a second potential stem sequence within the nucleic acid sequence; and f. comparing the nucleotides in the first and second potential stem sequences to determine whether the minimum number of base pairs exists within the first and second potential stem sequences.

2. A method as recited in claim 1, wherein at least the step of comparing the nucleotides in the first and second potential stem sequences is conducted with a computer.

3. A method as recited in claim 2, wherein at least the step of comparing the nucleotides in the first and second potential stem sequences is conducted with the use of computer code residing in a memory structure and operating upon a CPU of the computer.

4. A method as recited in claim 1, wherein the existence of potential base pairs in the first and second potential stem sequences is determined with the use of a matrix of potential bond values.

5. A method as recited in claim 1, further comprising incrementing the second potential stem sequence to omit a first nucleotide therein and to include an adjacent nucleotide in the nucleic acid sequence, and comparing the first potential stem sequence to the incremented second potential stem sequence.

6. A method as recited in claim 5, further comprising conducting the steps of incrementing the second potential stem sequence and comparing the first potential stem sequence to the incremented second potential stem sequence a number of times substantially equal to the number of nucleotides in the maximum loop size.

7. A method as recited in claim 6, further comprising, after conducting the steps of incrementing the second potential stem sequence and comparing the first potential stem sequence to the incremented second potential stem sequence a number of times substantially equal to the number of nucleotides in the maximum loop size, incrementing the first potential stem sequence, and repeating the process until substantially the entire contents of the nucleic acid sequence has been included in the comparison step.

8. A method as recited in claim 6, further comprising comparing the nucleotides in a located R-structure for potential wing structures within the R-structure.

9. A memory device comprising thereon computer instructions for operating within the CPU of a computer to conduct a process comprising:

a. obtaining a nucleic acid sequence;

b. defining a minimum number of base pairs in an R-structure to be identified;

c. establishing a maximum loop size of the R-structure to be identified;

d. identifying a first potential stem sequence within the nucleic acid sequence, said first potential stem sequence comprising a plurality of nucleotides;

e. identifying a second potential stem sequence within the nucleic acid sequence, said second potential stem sequence comprising a plurality of nucleotides;

f. comparing the nucleotides in the first and second potential stem sequences to determine a number of base pairs that can be formed between the first and second potential stem sequences; and g. determining whether the number of base pairs that can be formed is greater than or equal to the minimum number of base pairs.

10. A memory device as recited in claim 9, wherein the number of base pairs that can be formed is determined with the use of a matrix of potential bond values.

11. A memory device as recited in claim 9, further comprising incrementing the second potential stem sequence to omit a first nucleotide therein and to include an adjacent nucleotide in the nucleic acid sequence, and comparing the first potential stem sequence to the incremented second potential stem sequence.

12. A memory device as recited in claim 11, further comprising incrementing the second potential stem sequence and comparing the first potential stem sequence to the incremented second potential stem sequence a number of times substantially equal to the number of nucleotides in the maximum loop size.

13. A memory device as recited in claim 12, further comprising, after conducting the steps of incrementing the second potential stem sequence and comparing the first potential stem sequence to the incremented second potential stem sequence a number of times substantially equal to the number of nucleotides in the maximum loop size, incrementing the first potential stem sequence, and repeating the process until substantially the entire contents of the nucleic acid sequence has been included in the comparison step.

14. A memory device as recited in claim 12, further comprising comparing the nucleotides in a located R-structure for potential wing structures within the R-structure.

15. A memory device comprising thereon computer program instructions for creating data structures and data operator modules comprising:

a. an interface module for interfacing with a human operator;

b. a data loading module for loading selected nucleic acid sequences;

c. a hairpin locator module for locating R-structures within a selected nucleic acid sequence, the hairpin locator module comprising therein:

i. a base pair identifier module, and ii. a potential bond counter to keep track of potential identified bonds;

d. a wing locator module for locating wings within R-structures; and e. an R-structure organizer for organizing located R-structures.

* * * * *